US011519018B2

(12) United States Patent
De Manzanos Guinot et al.

(10) Patent No.: US 11,519,018 B2
(45) Date of Patent: Dec. 6, 2022

(54) IN SITU DETECTION OF MICROORGANISMS

(71) Applicant: FungiAlert Limited, Harpenden (GB)

(72) Inventors: Angela De Manzanos Guinot, Harpenden (GB); Kerry O'Donnelly Weaver, Harpenden (GB)

(73) Assignee: FUNGIALERT LTD., Harpenden (GB)

( * ) Notice: Subject to any disclaimer, the term of this patent is extended or adjusted under 35 U.S.C. 154(b) by 201 days.

(21) Appl. No.: 16/305,620

(22) PCT Filed: Jun. 2, 2017

(86) PCT No.: PCT/EP2017/063450
§ 371 (c)(1),
(2) Date: Nov. 29, 2018

(87) PCT Pub. No.: WO2017/207756
PCT Pub. Date: Dec. 7, 2017

(65) Prior Publication Data
US 2020/0332339 A1 Oct. 22, 2020

(30) Foreign Application Priority Data
Jun. 2, 2016 (GB) .................. 1609671

(51) Int. Cl.
*C12Q 1/24* (2006.01)
*C12Q 1/04* (2006.01)
(52) U.S. Cl.
CPC .......... *C12Q 1/24* (2013.01); *C12Q 1/04* (2013.01); *G01N 2333/37* (2013.01)
(58) Field of Classification Search
CPC ........ A61K 35/60; A61K 8/987; A61K 8/676; A61K 8/982; A61K 2800/24; A61K 2800/805; A61K 2800/84; A61K 35/54; A61K 35/57; A61K 35/655; A61K 9/0014; A61K 49/0008; A61K 49/006; A61K 49/0021; A61K 47/60; A61K 47/64; A61K 49/0043; A61K 49/0056; A61K 49/223; A61K 51/088; A61K 2039/505; A61K 2039/507; A61K 39/3955; A61K 45/06; A61K 2300/00; A61K 31/553; A61K 31/573; A61K 47/6957; A61K 9/0019; A61K 9/0051; A61K 9/1647; A61Q 19/00; A61Q 19/02; A61Q 19/08; A61Q 7/00; A61Q 11/00; A61Q 19/005; A61Q 19/007; A61Q 19/008; A61Q 1/04; C12Q 1/24; C12Q 1/04; G01N 2333/37; G01N 2333/4603; G01N 2510/00; G01N 33/5014; G01N 33/5088; G01N 15/1484; G01N 2015/0288; G01N 2015/149; G01N 2015/1493; G01N 33/558; G01N 33/5302; G01N 2015/008; G01N 33/4833; G01N 33/543; G01N 33/54306; G01N 15/1456; G01N 15/1468; G01N 2015/1075; G01N 27/622; G01N 27/624; G01N 27/64; G01N 35/00; G01N 33/5306; G01N 33/54373; A61P 17/02; A61P 35/00; A61P 13/12; A61P 1/16; A01K 2217/05; A01K 2227/40; A01K 2267/0393; A01K 2267/035; C12N 15/8509; B01L 3/502738; B01L 2200/12; B01L 2200/0636; B01L 2200/0647; B01L 2200/0652; B01L 2200/0668; B01L 2200/10; B01L 2300/0645; B01L 2300/0681; B01L 2300/0861; B01L 2300/0867; B01L 2300/087; B01L 2300/0887; B01L 2300/123; B01L 2400/0409; B01L 2400/0481; B01L 2400/0655; B01L 3/502746; B01L 3/502753; B01L 3/502761; B01L 3/5023; B01L 2200/027; B01L 2400/0633; B01L 3/502715; B01L 2200/16; B01L 2300/06; B01L 2300/0636; B01L 2300/088; B01L 2300/0893; B01L 2400/0415; B01L 2400/0622; B01L 2200/0621;
(Continued)

(56) References Cited
U.S. PATENT DOCUMENTS 5,817,472 A 10/1998 Hardham et al.
7,947,224 B2 * 5/2011 Tashiro .................. G01N 1/405
359/585
(Continued)

FOREIGN PATENT DOCUMENTS

GB 2533332 A 6/2016
WO 94/08042 A1 4/1994
(Continued)

OTHER PUBLICATIONS

Arvidson et al. Cultivation Media for Bacteria. https://learn.chm.msu.edu/vibl/content/differential/. 2013;1-2.*
(Continued)

*Primary Examiner* — Lynn Y Fan
(74) *Attorney, Agent, or Firm* — The Dobrusin Law Firm, P.C.; Bryan S. Lemanski

(57) ABSTRACT

A system for the detection of pathogenic organisms in growth substrate or water is described which comprises means for the delivery of an attractant into the growth substrate or water, means for directing the microorganism to a detector for the detection of the microorganism of interest, and a detector which provides a signal when the microorganism of interest is detected, the use of the system in agriculture and horticulture is also described.

20 Claims, 1 Drawing Sheet

(58) Field of Classification Search
CPC ..... B01L 2300/0825; B01L 2400/0677; B01L 2300/069; B01L 2300/0819; B01L 3/5085; C12M 1/34; C12M 21/06; C12M 23/16; C12M 1/12; C12M 1/123; C12M 1/18; G02B 21/32; A01N 41/02; A01N 25/04; A01N 31/02; A01N 37/02; A01N 37/06; Y02A 50/30; Y02A 50/51; Y02A 50/53; Y02A 50/60; Y10T 436/25; Y10T 436/11; Y10T 436/2575; B01J 2219/00576; B01J 2219/00648; B01J 2219/00725; B01J 2219/0074; B01J 2219/00743; B01J 2219/00639; B01J 2219/00659; B01J 2219/00664; B01J 2219/0072; B82Y 30/00; B82Y 5/00; C07K 7/08; C07K 7/64; C07K 16/22; C07K 16/2818; C07K 2317/21; C07K 2317/30; C07K 2317/77; C07K 2317/92; Y10S 435/805; Y10S 435/81; Y10S 435/97; Y10S 436/81; A61B 17/12022; A61B 17/11; A61B 17/1219; A61B 17/00491; A61B 17/0057; A61B 17/12118; A61B 17/12181; A61B 17/3468; A61B 18/18; A61B 2017/00411; A61B 2017/0065; A61B 2017/00876; A61B 2017/1205; A61B 18/04; A61B 2017/00544; A61B 2017/22001; A61B 18/02; A61B 18/1492; A61B 18/245; A61B 2017/00809; A61B 2018/00005; A61B 2018/00023; A61B 2018/00345; A61B 2018/00517; A61B 2018/00541; A61B 2018/00577; A61B 2018/00595; A61B 2018/00982; A61B 2018/1861; A61B 2218/002; A61F 2250/0067; A61F 2/82; A61F 2250/0068; A61F 2/0077; A61F 2002/9528; A61F 2210/009; A61F 2/013; A61F 2/95; A61L 2300/404; A61L 2300/406; A61L 2300/416; A61L 2300/426; A61L 2300/432; A61L 31/16; A61N 1/05; A61N 2005/1011; A61N 7/00; A61M 37/00

See application file for complete search history.

(56) References Cited

U.S. PATENT DOCUMENTS

| | | | |
|---|---|---|---|
| 2004/0033555 A1* | 2/2004 | Anderson | C12Q 1/18 435/34 |
| 2007/0202137 A1* | 8/2007 | Ingham | B01L 3/5085 424/405 |
| 2007/0212681 A1* | 9/2007 | Shapiro | G01N 33/54373 435/5 |
| 2011/0275112 A1 | 11/2011 | Sarver, Jr. et al. | |
| 2013/0230846 A1* | 9/2013 | Babu | B01L 3/5023 435/5 |
| 2013/0334042 A1 | 12/2013 | Grieve et al. | |
| 2017/0349931 A1* | 12/2017 | Weaver | C12Q 1/04 |

FOREIGN PATENT DOCUMENTS

| | | |
|---|---|---|
| WO | 2011/139263 A1 | 11/2011 |
| WO | 2016/097726 A1 | 6/2016 |

OTHER PUBLICATIONS

PCT International Preliminary Report on Patentability dated Dec. 13, 2018, Application No. PCT/EP2017/063450.

International Search Report and Written Opinion from the European Patent Office for Application No. PCTZEP2017/063450, dated Sep. 13, 2017.

UK Search Report for Application No. GB1609671.1, dated Feb. 27, 2017.

Reid et al., Calcium Dependent, Genus-Specific, Autoaggregation of Zoospores of Phytopathogenic Fungi, Experimental Mycology, vol. 19, No. 3, pp. 202-213, Sep. 30, 1995.

Cahill et al., Exploitation of Zoospore Taxis in the Development of a Novel Dispstick Immunoassay for the Specific Detection of Phytophtora Cinnamomi, Phytopathology, vol. 84, No. 2, pp. 193-200, 1994.

Radajewski et al., Motility Responses and Desiccation Survival of Zoospores from the *Actinomycete kineosporia* sp. Strain SR11, Microbial Ecology, vol. 41, No. 3, pp. 233-244, Feb. 2001.

Tyler, Molecular Basis of Recognition Between Phytophtora Pathogens and Their Hosts, Annu. Rev. Phytophathology, vol. 40, pp. 137-167, Sep. 2002.

Jeffers et al., Comparison of Two Media Selective for *Phytophthora* and *Pythium* Species, Plant Disease, vol. 70, No. 11, Nov. 1986.

Guo et al., Two Widely Accessible Media for Growth and Reproduction of *Phytophthora* and *Pythium* Species, Applied and Environmental Microbiology, vol. 59, No. 7, pp. 2323-2325, Jul. 1993.

* cited by examiner

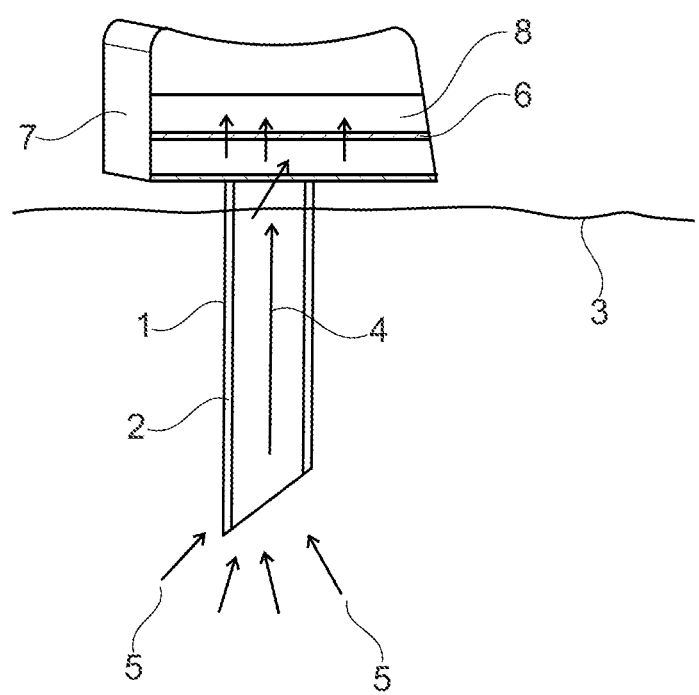

IN SITU DETECTION OF MICROORGANISMS

CROSS-REFERENCE TO RELATED APPLICATIONS

This application claims benefit to International Patent Application No. PCT/EP2017/063450, filed on Jun. 2, 2017, which claims benefit to GB 1609671.1, filed on Jun. 2, 2016, both of which are incorporated herein in their entirety.

FIELD

The present invention relates to the detection of microorganisms including pests and other microorganisms (such as fungi, oomycetes, bacteria and nematodes) in a growth substrate and/or water. In particular it relates to the detection of plant pathogens in a growth substrate and/or water and in particular to the detection of pests and organisms that cause disease in plants in situ in the field or areas where products are being grown on a commercial basis or in their natural environment. The invention is also concerned with equipment that may be used in such a detection.

BACKGROUND

Although the invention is primarily concerned with the early detection of microorganisms that have the potential to cause damage to plants it can also be used to detect the presence of microorganisms such as photosynthetic bacteria (such as *Rhodopseudomonas palustris* and *Rhodobacter sphaeroides*), lacto bacteria (such as *Lactobacillus plantarum* and *casei*, and *Streptococcus*), yeasts (such as *Saccharomyces* spp.), actinomycetes (such as *Streptomyces* spp.), $N_2$ fixing bacteria (such as *Rhizobium, Bradyrhizobium, Ensifer* and *Mesorhizobiu*), Mycorrhizae and phosphate solubilising microorganisms (such as bacteria (*Bacillus*) and fungi (*Aspergillus, Penicillium* spp.)), plant growth-promoting rhizobacteria, and probiotics for plants (such as *Pseudomonas*). These microorganisms can be beneficial to the health of plants to provide information to the grower concerning the need or otherwise to provide materials to enhance the well being of the plant in question.

Loss of plant yield due to plant disease from microorganisms including pathogens such as fungi, oomycetes, bacteria, nematodes and damaging insects is a global concern, not only in agriculture and horticulture but also in forestation, garden centres, private gardens and ornamental plants. Many valuable crops and ornamental plants are very susceptible to disease and would have difficulty surviving in nature without human intervention. Loss of products reared in water such as fish farms in lakes is also of concern.

Cultivated plants are often more susceptible to disease than their wild relatives because large numbers of the same species or variety (which have a uniform genetic background), are grown closely together, sometimes over many thousands of square kilometres. Disease caused by pathogenic organisms may spread rapidly under these conditions. For example, *Phytophthora*, a plant pathogen that generates spores that attack the roots and stems of a range of plants, vegetable and fruits, is of particular concern to growers as it can contaminate water supplies and can also stay undetected in plant debris and soil for many years. It is estimated that *Phytophthora*, known as the "Plant Destroyer of the $21^{st}$ Century", alone causes a $2-7 billion loss per crop per year worldwide (Roy et al, 2012 Review of Plant Pathology, Vol 6).

Numerous methods exist to detect plant disease. For example in the detection of plant pathogenic species, farmers typically use consultant agronomists who take a sample of soil or plant material, for example the leaf or root, and analyse the sample for the presence of plant pathogens. Analysis is conducted externally using laboratory tests. Such laboratory tests can include molecular techniques such as ELISA, PCR (PCR and real-time PCR), immunofluorescence (IF), flow cytometry, fluorescence in situ hybridization (FISH), and DNA microarrays. There are several problems with external laboratory testing of samples. Firstly, soil sampling selects only a small sample and may not necessarily reflect the true condition of the soil.

In some cases, the level of pathogenic organisms in the soil will be too low for detection, therefore in sampling an isolated area of soil the level of plant pathogen will be ineffective despite the presence of damaging amounts of the pathogen. External laboratory analysis requires transportation of samples away from the testing site to a laboratory and therefore there is a delay in providing the result of the diagnostic analysis. Any delay in detecting an organism which can cause disease in a plant, such as a plant pathogen, can lead to a spread of the disease and a greater number of plants being affected.

Samples can also be tested for the presence of pathogenic organisms using on-site lateral flow devices. Such devices require the farmer to take a sample from a plant, for example a leaf. The device extracts proteins in the plant sample and the presence of a plant pathogen can be detected. Each plant sample is representative only for the plant being tested. Each sample is therefore not representative of the entire plant growth area. Further, a plant sample that tests positive for a plant pathogen indicates the plant has already been affected by the pathogen. This may be too late to prevent damage due to the pathogen and also too late to prevent spread of the plant pathogen to surrounding plants.

Frequently, the farmer may not test for the presence of diseases at all and simply utilises preventative spraying routines against common diseases. It is not known if the plants will be targeted by a plant pathogen if left untreated and therefore such spraying routines may be unnecessary in some cases and involve the unnecessary use of chemicals having an adverse environmental impact, incur an unnecessary cost and may result in the pathogen becoming resistant to the treatment.

Early detection of threats to plant health and disease such as pests and plant diseases, caused by microorganisms, such as fungi, oomycetes, bacteria, and nematodes could facilitate the control of disease through proper crop management strategies such as vector control through pesticide applications, fungicide applications and disease-specific chemical applications and bio-controls. Additionally early detection in nurseries would enable the production and supply of disease free plants. There is therefore a need to provide an accurate and simple method and device for detecting these undesirable pathogenic species in soil or water that can be utilised at the site of plant growth or potential plant growth or water supply.

SUMMARY

In our PCT Application PCT/GB2015054036 we describe a device for detecting plant pathogen spores in soil or water particularly for detecting prior to the pathogen impacting the plant and this application contains a list of pathogens and this invention is inter alia applicable to the pathogens listed in that application.

United States Patent Publication 2013/0334042 describes the detection of airborne pathogen spores in situ in fields however this procedure requires considerable time for analysis to detect the pathogen and furthermore the detection generally occurs after at least some of the plants have been infected. Furthermore, the technique cannot be used to detect pathogenic microorganisms in soil or water.

Some pathogenic species, such as fungi, oomycetes and bacteria, may exist and be dormant for long periods of time in both soil and water and they can be activated by environmental changes such as rain, heat or other weather related issues. Once activated they can come into contact with vegetation, typically the roots of vegetation where they can enter into the vegetation and cause considerable damage to the particular crop. The vegetation may comprise the entire range of agricultural and horticultural crops, fruit crops such as orchards and vineyards, flower production, garden centres and ornamental gardens plants and trees growing in their natural environment such as in forests. The invention may be used for early detection of organisms which cause plant diseases, such as pathogenic microorganisms (fungi, oomycetes and bacteria), in nurseries where plants are grown for supply enabling greater confidence that the young plants are disease free. Pathogenic organisms may also exist in water systems such as water used for irrigation, aquifers, water gardens, reservoirs, tanks and lakes providing fish farms.

PCT Publication WO 94/08042 describes *Phytophthora cinnamomi* rands as one of the most important plant pathogens found throughout the tropical and temperate zones and this invention is particularly useful with *Phytophthora* type pathogens. These affect an increasingly diverse range of species from a wide variety of plant families. Hosts include agricultural crops such as vegetables and arable crops and also important horticultural crops such as citrus fruit, avocado, pineapple and macadamia, ornamental species and several valuable timber species. Effects of this can be devastating examples of the impact of an introduced pathogen on a flora composed of many susceptible species. Control of this pathogen and improved understanding of its biology must be based in part on information on the location and density of inoculum in soil. However, the detection proposed in WO 94/08042 requires attracting spores, growing the spores in the laboratory for subsequent detection. Accordingly the detection takes several days to accomplish and it is not performed in situ and requires sample manipulation and a laboratory with qualified personnel.

Whilst the present invention is generally applicable to the identification of any microorganisms in a growth substrate and/or water it is particularly concerned with the detection of pathogens and especially the detection of *Phytophthora* based pathogens.

The present invention therefore provides the detection of microorganisms and particularly disease causing organisms such as pathogenic fungi, oomycetes, bacteria and pests in a growth substrate and/or water supporting or designed to support vegetation in its natural environment and/or on a commercial site by providing an attractant for the microorganisms within the growth substrate and/or water wherein the attractant attracts the microorganism, and directs it to a detector which directly provides an indication of the presence of the microorganism.

The invention further provides a system for the detection of microorganisms and particularly disease causing organisms in a growth substrate and/or water comprising means for the delivery of an attractant into the growth substrate and or water, means for directing the microorganism that are attracted by the attractant to a detector, and a detector which provides a signal when a microorganism of interest is detected.

BRIEF DESCRIPTION OF THE DRAWINGS

FIG. 1 illustrates a perspective view of a detection device in accordance with the present teachings.

DETAILED SPECIFICATION

The term "growth substrate" includes any natural and synthetic substrates in which plants may be grown and includes soil, coir, peat, sand and mixtures thereof.

As used herein, the term "attractant" includes any substance which encourages the growth of the microorganism to be detected which may be a plant disease or disease causing species or a plant damaging pest. The attractant can be the growth media or a component of the growth media, and the attractant will be selected according to the microorganism of interest. In one embodiment the attractant is a chemoattractant and particularly a plant pathogen chemoattractant. The attractant can be selected from amino acids or alcohols, plant extract or specific plant compounds such as phytohormones, plant proteins or plant signalling compounds, sugars, organic acids, phenolics or other proteins such as casein, pectin and any derivatives of these may also be used as attractants. The attraction may also be an electrostatic or ionic attraction and we have found that divalent metals particularly calcium are useful components of attractants. The choice of attractant will depend upon the microorganism such as the disease or disease causing organism that is to be detected. In the detection of motile pathogenic spores we prefer to use a mixture of two or more chemoattractants although in certain embodiments one can be used effectively.

The attractant for directing the microorganisms to the detector preferably comprises a growth medium for the microorganism which is provided in a manner that both encourages growth of the microorganism and directs the microorganism to the detector. For example, the invention may be implemented by a device comprising a hollow probe, tube or needle designed to be placed within the growth substrate and/or water connected to a compartment that holds the detector. At least part of the inner surface of the hollow probe, tube or needle may be coated with a growth medium such as an agar medium and the pattern of the coating may be such that it encourages the microorganism to move towards the detector compartment as it grows on the medium.

For example, where the device is configured so that in use the detector compartment is positioned at the top end of the hollow probe, tube or needle and the bottom end of the hollow probe, tube or needle is configured to be within the growth substrate and/or water if the growth medium is provided as a vertical strip on the inner surface of the hollow probe, tube or needle it will encourage the microorganism to move upwards along the strip and into the detector compartment.

The growth medium employed will depend upon the nature of the microorganism that is to be detected. In certain instances it may comprise or contain a chemoattractant for the microorganism to be detected. The growth medium may also contain ingredients such as fungicides or antibacterial agents which can destroy or reduce the amount of microorganisms entering the detector and which are not the microorganism which is to be detected.

The attractant growth medium used in this invention will attract specific microorganism(s) which will then travel through the hollow, probe, tube or needle to the detector. The attractant is a growth medium which aids growth of the microorganism(s) and can have many different compositions, depending on the microorganism(s) being detected. Examples of suitable growth media are described in Jeffers and Martin (*Plant Disease*, 1986, Vol. 80 No. 11) and Guo and Ko (*Applied Environmental Microbiology*, July 1993, Vol. 59, No. 7, p 2323-2325).

In one embodiment the growth medium comprises antibiotics and/or nutrients. The presence of antibiotics can prevent growth of undesirable bacteria. In another embodiment the culture medium comprises pesticides or fungicides and the presence of antibiotics, pesticides and/or fungicides allows the growth of the microorganism of interest and prevents the growth of microorganism not of interest, for example other fungi and bacteria that may have entered the hollow probe, tube or needle of the device. In one embodiment the growth medium comprises nitrobenzenes or isoflavonoids. The growth medium can contain any combination of agar, nutrients, alcohols, amino acids, fungicides, pesticides, antibiotics, nitrobenzenes, plant extracts and/or isoflavonoids.

In one embodiment the growth medium in the hollow tube, probe or needle is at a lower concentration than the growth medium in the detector which encourages the microorganism to move into the detector. The growth medium may additionally comprise a buffer which maintains the pH of the medium in the hollow tube, probe or needle. Where a growth medium is also present in the detector it may also comprise a buffer which may be at a lower concentration than the buffer in the medium in the hollow tube, probe or needle. The lower concentration of buffer in the detector means that the pH level of the medium in the detector can be altered. In one embodiment the growth medium in the hollow tube, probe or needle comprises a buffer and the growth medium in the detector does not comprise a buffer. The absence of buffer in the detector means that the pH level of the medium can be altered. These embodiments are particularly useful when the detection means is a pH indicator. The person skilled in the art will be able to select an appropriate buffer from commercially available buffers. In one embodiment the buffer is optimal for the survival of *Phytophthora*.

The person skilled in the art will be able to select an appropriate growth medium from commercially available culture media. Further, the person skilled in the art will be able to synthesize an appropriate culture medium from standard literature protocols.

In one embodiment the growth media are agar culture media.

As indicated in a preferred embodiment the detector also includes a growth medium for the microorganism which enables the organism to multiply to provide a high enough concentration for detection. The time required for multiplication varies according to the nature of the organism to be detected but we have found that using the techniques of this invention it can be accomplished more quickly than with currently existing techniques, and this invention offers a simple in-situ detection device, that does not require sample manipulation or qualified personnel for detection.

The invention is applicable to any microorganisms including any type of spore produced by a disease causing organism, such as fungi, oomcyete, and bacteria, including bacterial spores and motile spores such as zoospores. Detection of zoospores is one embodiment of the use of the present invention.

In one embodiment the present invention is applicable to the detection of any plant pathogens including at least one species of *Phytophthora*. "*Phytophthora*" includes all the species of the genus *Phytophthora*.

Other pathogens to which the invention may be applied include *Magnaporthe, Botrytis, Cochiliobolus, Puccinia, Gymnosporangium, Hemileia*, and all the species of the genus *Fusarium*.

Further pathogenic organisms to which the invention may be applied include *Gibberella, Blumeria, Mycosphaerella, Colletotrichum, Sphacelotheca, Sporisorium, Ustilaginoidea, Ustilago, Melampsora, Pythium*, including all the species of the *Pythium, Achyla, Aphanomyces, Albugo, Wilsoniana, Basidiophora, Bremia, Alternaria, Pseudopezicula, Cercospora, Elsinoë, Sphaceloma, Armillaria mellea, Rhizomorpha, Diplocarpon, Marssonia, Erysiphe, Plasmopara, Guignardia, Colletotrichum, Glomerella, Stemphylium, Pleospora, Ulocladium, Stemphylium, Thielaviopsis, Chalara, Pseudocercospora, Macrophomina, Macrophoma, Vaccinium, Pyrenochaeta, Didymella, Stemphylium, Botryotinia, Fulvia, Mycovellosiella, Cladosporium, Passalora, Phom, Oidiopsis, Leveillula, Cochliobolus, Curvularia, Rhizoctonia, Bipolaris, Waitea, Thanatephorus, Corticium, Rhizopus, Septoria, Geotrichum, Galactomyces, Sclerotinia, Sclerotium, Athelia, Corynespora, Verticillium, Acremonium, Cephalosporium, Lasiodiplodia, Botryodiplodia, Physoderma, Physalospora, Diplodia, Botryosphaeria, Stenocarpella, Sclerophthora, Sclerospora, Peronosclerospora, Nigrospora, Khuskia, Trichoderma, Hypocrea, Phyllachora, Botryotinia, Cunninghamella, Doratomyces, Cephalotrichum, Gonatobotrys, Pithomyces, Scopulariopsis, Claviceps, Sphacelia, Phyllosticta, Mycosphaerella, Gloeocercospora, Kabatiella, Exserohilum, Helminthosporium, Setosphaeria, Hyalothyridium, Ascochyta, Bipolaris, Epicoccum, Drechslera, Graphium, Leptosphaeria, Ophiosphaerella, Scolecosporiella, Paraphaeosphaeria, Phoma, Septoria, Penicillium, Phaeocytostroma, Sphaerulina, Dictochaeta, Microdochium, Mucor, Mariannaea, Periconia, Physopella, Rhopographus, Spicaria, Angiopsora, Nectria phomopsis, Spicaria, Selenophoma, Gaeumannomyces, Myrothecium, Monascus, Bremiella, Pseudoperonospora, Rhizophydium, Synchytrium, Olpidium, Ligniera, Plasmidiophora, Polymixia, Sorodiscus, Sorosphaera, Spongospora, Tetramyxa* and *Aspergillus*.

The attractant may be provided on a carrier upon which the attractant is absorbed. In a preferred embodiment the device of the present invention includes a hollow probe, tube or needle which is inserted into the growth substrate or water and the attractant is provided on a semi gel material by which it adheres to the inside of the hollow tube, probe or needle of the device upon which the disease forming species colonises and travels upwards. Further examples of carriers for the attractant include films or membranes such as polyamide or nitrocellulose films. The film or membrane may be an electrostatically charged membrane. The film or membrane may be provided on the interior surface of a hollow tube, probe or needle which extends into the growth substrate or water and provides a delivery mechanism for the microorganism usually a disease causing organism from the growth substrate or water to the detector. In one embodiment, the attractant is provided in a manner that enables at least some of it to leach out from the hollow tube, probe or needle into the growth substrate or water, for example the attractant may be a mixture of two or more attractants each having a different solubility or miscibility with the growth substrate or water. In this way some chemoattractant can be leached out into the growth substrate or water to attract the disease causing organism and some will remain in the hollow tube, probe or needle and so direct the disease causing organism through the hollow tube, probe or needle to the detector.

The attractant composition can perform the triple function that firstly it attracts the microorganism into the device, secondly it directs the microorganism into the detector and thirdly it can cause the microorganism to grow as it moves towards the detector. In a further preferred embodiment the attractant composition can contain ingredients which perform a fourth function of destroying or reducing the amount of microorganisms that are present other than those to be detected and so limiting their ability to enter the detector and impair its function.

Where plant pathogens are to be detected and a plant pathogen chemoattractant is used as the attractant it will typically be specific for the plant disease causing species to be detected and as described more than one attractant may be used. The attractants may be specific for one type of disease causing species such as a particular plant pathogen or alternatively the attractant may attract more than one type of plant disease causing microorganism. In one embodiment, a plant pathogen attractant is used that is specific for several different plant pathogens. Alternatively the different plant pathogen attractants used may be specific for different plant pathogens i.e., the specificity of the chemoattractant may be chosen such that they do not overlap. Suitable plant pathogen chemoattractants are known in the art. However we have found that certain attractants or mixtures of attractants allow more rapid capture, direction and detection of the pathogens and the use of those materials is a further embodiment of this invention. Typically, each plant pathogen attractant used is specific for the same plant pathogen.

In one embodiment where the attractant is a chemoattractant at least one plant pathogen chemoattractant is a chemoattractant for *Phytophthora*. Examples of chemoattractants for *Phytophthora cinnamomi* are described in Cahill and Hardman (Phytopathology, Vol 84, No 2, pages 193-200). In one embodiment at least one plant pathogen attractant attracts one or more species of *Phytophthora*. In some embodiments at least one plant pathogen chemoattractant can attract more than one plant pathogen. In one embodiment at least one plant pathogen chemoattractant attracts one or more species of *Phytophthora* and one or more other plant pathogens.

In one embodiment where the attractant formulation is provided within a hollow tube, probe or needle, the tube should be robust and resistant to corrosion in growth substrate and water. Plastic probes or tubes being particularly useful. The attractant should be provided in an amount such that if, as is preferred some of the attractant has leached out from the tube or probe into the growth substrate or water the attractant remaining in the tube or probe is in a concentration gradient wherein the attractant is present at a higher concentration near to the detector than at the end of the means that introduces the attractant into the growth substrate or water. In other words, the concentration is lower at the end of the delivery means that will be in contact with the growth substrate or water when in use than at the end which delivers the microorganism to the detector and this concentration gradient may be provided initially or it may be formed in situ during operation of the detection system. Although not essential such a gradient can assist in causing the microorganism to be carried up the hollow tube, probe or needle into the detector.

In a preferred embodiment the attractant is provided on the internal surface of one or more hollow probes, tubes or needles that are designed to extend into the growth substrate or water of concern to introduce the attractant into the growth substrate or water. The attractant may be attached to the inside of the hollow tubes, probes or needles by incorporation within a gel like material. The one or more hollow tubes, probes, or needles may be pointed to help with insertion into soil and may be of an internal diameter such that as the microorganism grows by contact with the attractant it can pass upwardly along the bore of the probe(s), tube(s) or needle(s). Alternatively the attractant may be held inside the hollow tube, probe or needle by a membrane which can release at least some of attractant into the growth substrate or water. The detector may then be provided at the end of the hollow probe, tube or needle remote from the growth substrate or water so that in use the disease causing species pass through the hollow tube, probe or needle into the detector system. The disease causing species are attracted by the attractant into and up the hollow tube, probe or needle until it reaches the detector system which will issue a signal when a particular microorganism is identified. Where several hollow probes, tubes or needles are employed they are preferably channelled to feed into a single detector or each may have its own detector.

The size and shape including the cross section of the hollow tube, probe or needle can be selected according to the location in which the detection device is to be used and also the nature of the microorganism to be detected. The thickness location and concentration of the coating of the attractant on the inner surface of the hollow tube, probe or needle will also be selected according to the nature of the microorganism to be detected. We have found that hollow tubes, probes or needles of from 4 to 10 cm long with a cross sectional area of from 0.5 to 5 sq cm are particularly useful and that coatings of the attractant of thickness from 0.1 to 1 cm particularly 0.2 to 0.5 cm are very effective.

When used in a growth substrate the attractant should not be inactivated by the growth substrate and materials contained therein. It should also be stable in the temperature ranges experienced in the particular environment in which it is used. When used in a growth substrate it should have some solubility in the moisture contained in the growth substrate and when used in water it should be selected to have the required solubility in water under the conditions in which it is used. Where the attractant is provided as a coating on the surface of a hollow probe, tube or needle such as being held in a gel or being absorbed on a carrier such as a film or membrane attached to the inner surface of the hollow probe, tube or needle it may be releasable into the growth substrate or water to attract the microorganism whilst also being retained on the inner surface of the tube or probe to direct the microorganism to the detector. This may be accomplished by providing the attractant as two or more layers on the inner surface of the hollow tube, probe or needle. It is however important that sufficient attractant remains on the inner surface of the hollow tube, probe or needle.

We have found that amino acids and/or $C_1$ to $C_4$ monohydric alcohols and mixtures thereof as well as divalent metals particularly calcium are particularly useful attractants and they also act as chemoattractants particularly for the spores of *Phytophthora*. We have also found that they may conveniently be provided on a membrane such as a nylon or nitro cellulose membrane or in a gel such as agar.

In operation of this invention with disease causing microorganisms once active the disease causing organism within the growth substrate or water will be attracted by the attractant and will move or grow towards the attractant which is provided in a manner that then directs the microorganism towards the detector typically through the hollow tube, probe or needle. In this way the presence of the disease causing organism can be detected before it has significant interaction with the particular vegetation allowing remedial action to be taken before the disease causing organism causes significant damage to the vegetation.

The detector of the system of this invention can be a compartment configured for the detection of any particular microorganism. For example, in one embodiment it may comprise a filter system designed to permit the passage of the microorganism in question and to exclude other materials perhaps including other microorganism. Alternatively it may be a device programmed to selectively detect certain microorganism. In one embodiment of the invention an attractant for a disease causing organism is also included in the detector system to ensure that the disease causing organism is not only attracted to the hollow tube, probe or needle but is attracted to flow up the hollow tube, probe or needle and into the detection system. In this instance the attractant can be provided in gradually increasing amounts within the hollow tube, probe or needle and also within the detector compartment to ensure that the organism is directed towards the detector.

Although optional, in one embodiment the detector material employed in the invention comprises a filter and a growth medium in which the microorganism can multiply. The medium can be selective according to the particular microorganism to be detected. When a filter is used it selectively allows the microorganism being detected to reach the growth medium within the detector and prevents species of different shapes and sizes from reaching the medium in the detector. By using a selective filter in combination with attractant(s) for a specific microorganisms of interest the device can detect a microorganisms of interest. A filter with pores of 1 to 100 µm has been found particularly useful for *Phytophthora*. In other embodiments, the filter may be omitted and this has been found in some situations to enable more rapid detection. In a preferred embodiment there is chemical or biological filtration by the provision of antibiotics and antifungals preferably within the attractant formulation provided on the inner surface of the tube, probe or needle and optionally within the detector material.

The detector system may include a growth medium which enables the microorganisms that has been delivered to the detector to multiply. Suitable growth medium can include antibiotics and antifungals which can kill microorganisms other than those to be detected. The growth medium may also contain at least one attractant for the microorganism. The attractant will attract specific microorganisms so that they will travel through the filter if used and into the culture medium where the attractant is a chemoattractant this may be accomplished by chemotaxis. In some embodiments the growth medium can comprise additional chemoattractants. The growth medium stimulates the multiplication of the microorganisms which aids detection. The medium can have many different compositions, depending on the microorganism being detected, which will be well understood by the person skilled in the art. In one embodiment the culture medium is optional for the survival of *Phytophthora*. Examples of suitable media are described in Jeffers and Martin (Plant Disease, 1986, Vol 80 No 11) and Guo and Ko (Applied and Environmental Microbiology, July 1993, Vol 59, No 7, p 2323-2325).

In one embodiment, the detector and the delivery tube, probe or needle contain the same attractant. In a preferred embodiment the concentration of the attractant is higher in the detector than the concentration of attractant in the hollow tube, probe or needle attraction system. This creates a concentration gradient whereby the microorganism specifically attracted to the attractant will travel to the detection system.

The detector may indicate the presence of the microorganism in any suitable manner for example it may issue an audible and/or visible signal such as a flashing light, when the presence of a particular microorganism is detected. Alternatively it may issue a signal that is transmitted to the farmer or land or water owner at a remote location perhaps via a drone or a satellite. As a further alternative the culture medium employed in one embodiment of the invention can be of a material that indicates change such as a change in pH when the microorganism of choice is growing and may contain an indicator which undergoes a colour change when the pH changes. Alternatively or additionally the change in pH can be converted into a signal which can be used for remote sensing.

This invention as described may be implemented in agriculture and horticulture by placing one or more of the detector systems of this invention in the growth substrate or water adjacent to materials being grown therein. The optimum distance between detector systems in, for example, a field, will depend on the nature of the crop, the type of growth substrate, the prevailing climate etc. These can all be determined by trial and error although preliminary results suggest groups of devices such as that from 10 to 20 devices per hectare will be sufficient. In another embodiment the invention may be employed in freshly tilled growth substrate or available water systems to determine their suitability for public consumption or use and use in agriculture and horticulture and the need for addition of material such as fertilizers, pesticides, insecticides, fungicides and the like. The invention therefore further provides an array of detector systems of this invention distributed across a field or water system.

The invention is illustrated by reference to the accompanying FIG. 1, which shows a hollow probe or tube (1) carrying internally a layer (2) of an attractant for the microorganism of interest. The probe or tube passes down into growth substrate or water the surface of which is shown at (3). Some of the attractant leaches out into the growth substrate or water to attract the microorganism (5) which is directed into the hollow tube as indicated by the arrows and up the tube as shown by arrow (4). The microorganism grows during contact with the attractant and then passes into the detector (7) containing a filter (6) and a growth medium (8). The contents of the detector changes colour when the microorganism of interest is detected.

The invention is illustrated by reference to the following Example.

One strawberry plant out of ten strawberry plants, which were growing in substrate grow bags, was inoculated with *Phytophthora cactorum*. Devices, as shown in the attached FIGURE, were placed in the grow bags to monitor the distance a positive result could be detected from the infection site. The devices contained an internal layer coating of 0.2 cm of an agar growth media containing a mixture of four attractants, antifungals and antibiotics, and the detector contained a similar growth media as well as a pH indicator.

After 24-48 hours, all of the devices within the grow bag changed colour, indicating the *Phytophthora* had transferred from the substrate, up the tube, and into the detector.

The invention claimed is:

1. A system for the detection of microorganisms in a growth substrate or water comprising:
   (a) a hollow tube or a hollow needle that is inserted into the growth substrate or water;
   (b) a detector connected to the hollow tube or the hollow needle that signals when a microorganism of interest is present in the detector, wherein detection of the microorganism of interest is completed while the hollow tube or the hollow needle is inserted into the growth substrate or water; and
   (c) an attractant layer located on an interior surface of the hollow tube or the hollow needle, wherein a portion of an attractant within the attractant layer leaches out of the hollow tube or the hollow needle into the growth substrate or water to attract the microorganism into and through the hollow tube or the hollow needle, thereby directing the microorganism into the detector;
   wherein the detector is located at an end of the hollow tube or the hollow needle remote from and free of contact with the growth substrate or water.

2. The system according to claim 1, wherein the detector includes a growth medium that facilitates multiplying of the microorganism located within the detector.

3. The system according to claim 2, wherein the attractant is a chemoattractant for *Phytophthora*.

4. The system according to claim 1, wherein the attractant is selected from: amino acids; alcohols; plant extract or phytohormones; plant proteins or plant signaling compounds; sugars; organic acids; phenolics; casein; pectin; and calcium.

5. The system according to claim 1, wherein the attractant is provided as a layer that is located onto the interior surface of the hollow tube or the hollow needed.

6. The system according to claim 1, wherein the attractant layer has a higher concentration of the attractant nearer to the detector than at the end of the hollow tube or the hollow needle that introduces the attractant of the attractant layer into the growth substrate or water.

7. The system according to claim 1, wherein the detector includes a filter that permits passage of the microorganism of interest into the detector and excludes passage of other microorganisms.

8. The system according to claim 2, wherein the growth medium includes antibiotics and antifungals to kill microorganisms other than the microorganism of interest to be detected.

9. The system according to claim 2, wherein the growth medium employed in the detector provides a signal when the microorganism of interest is detected.

10. A process for the detection of microorganism in a growth substrate or water using the system of claim 1, comprising:
    (a) placing an open end of the hollow tube or the hollow needle into the growth substrate or water, thereby providing the attractant layer to attract the microorganism within the growth substrate or water, wherein the attractant layer attracts the microorganism and directs the microorganism upward through the hollow tube or the hollow needle towards the detector; and
    (b) detecting the microorganism of interest with the detector.

11. The process according to claim 10, wherein the detector includes at least one antibiotic or antifungal in a growth medium to allow the microorganism to multiply.

12. The process according to claim 10, wherein the attractant is selected from amino acids, alcohols, plant extract or phytohormones, plant proteins or plant signaling compounds, sugars, organic acids, phenolics, casein, pectin, and calcium.

13. The process according to claim 10, wherein the detector signals when the microorganism of interest is identified, and the signal is provided by the detector when the hollow tube or the hollow needle is still positioned within the growth substrate or water.

14. The system according to claim 2, wherein the growth medium of the detector changes color to provide the signal.

15. The system according to claim 8, wherein the growth medium is an agar culture medium.

16. The system according to claim 5, wherein the attractant layer is a semi gel material that adheres to the interior surface of the hollow tube or the hollow needle.

17. The system according to claim 2, wherein the growth medium also includes an attractant, and the attractant within the growth medium is the same as the attractant within the attractant layer.

18. The system according to claim 17, wherein a concentration of the attractant within the growth medium is higher than a concentration of the attractant within the attractant layer.

19. The system according to claim 18, wherein the growth medium, the attractant layer, or both include a buffer that maintains a pH level of the growth medium, the attractant layer, or both.

20. The system according to claim 2, wherein the attractant of the attractant layer is a mixture of two or more attractants each having a different solubility or miscibility with the growth substrate or water to facilitate partial leaching of the attractant into the growth substrate or water.

* * * * *